United States Patent [19]

Pierre et al.

[11] Patent Number: 4,595,467

[45] Date of Patent: Jun. 17, 1986

[54] PROCESS FOR PREPARATION OF GLYOXYLIC ACID THROUGH ELECTROCHEMICAL ANODIC OXIDATION OF GLYOXAL

[75] Inventors: Gérard Pierre, Eybans; Mokhlis E. Kordi; Georges Cauquis, both of Grenoble, all of France

[73] Assignee: Societe Francaise Hoechst, Puteaux, France

[21] Appl. No.: 759,886

[22] Filed: Jul. 29, 1985

[30] Foreign Application Priority Data

Sep. 4, 1984 [FR] France ................................ 84 13607
Nov. 28, 1984 [FR] France ................................ 84 18117

[51] Int. Cl.$^4$ ................................................ C25B 3/02
[52] U.S. Cl. ..................................................... 204/79
[58] Field of Search .......................................... 204/79

[56] References Cited

U.S. PATENT DOCUMENTS 4,235,684 11/1980 Harada et al. .......................... 204/79

FOREIGN PATENT DOCUMENTS 2443517 4/1980 France .................................. 204/79

OTHER PUBLICATIONS

Journal of the Electrochemical Society, vol. 130, No. 6, Jun. 1983, pp. 1305–1312, Manchester, N.H.; E. Leiva et al., "The Influence of Platinum Electrode Surface on the Electroadsorption and Electro-Oxidation of Methanol in Acid Solutions".

Chemical Abstracts, vol. 90, No. 24, 6/11/79, p. 515, Resume 194539j, Columbus, Ohio; G. Inzelt et al.; "Electrochemical Behavior of Ethylene Glycol and Its Oxidation Products on a Platinum Electrode.III. Effect of Chemisorption on the Kinetics of Oxidation of Glyoxal and Glyoxalic Acid".

*Primary Examiner*—Howard S. Williams
*Attorney, Agent, or Firm*—Sheridan Neimark

[57] ABSTRACT

Process for preparation of glyoxylic acid through electrochemical anodic oxidation of glyoxal in aqueous solution at a temperature comprised between 0° C. and 70° C. in an electrolyzer comprising at least one cathodic compartment containing a cathode and a catholyte, at least one anodic compartment containing an anode and an anolyte, consisting of an aqueous solution of glyoxal and an electrolyte, and at least one separator between both of these compartments. In such process the anode is doped by metallic adatoms selected from the group comprising silver, bismuth, copper, tin and thallium.

6 Claims, No Drawings

PROCESS FOR PREPARATION OF GLYOXYLIC ACID THROUGH ELECTROCHEMICAL ANODIC OXIDATION OF GLYOXAL

This invention relates to a process for preparation of glyoxylic acid through anodic electrochemical oxidation of glyoxal.

It is known to oxidize in aqueous medium glyoxal into glyoxylic acid either with nitric acid (French Pat. Nos. 1 326 605 to 2 372 141) or through electrochemical process (French patent application No. 2 443 517).

More generally, it is known that certain electrochemical processes permit to accede to glyoxylic acid such as cathodic reduction of oxalic acid (French patent No. 151 150), anodic oxidation of ethyleneglycol or tartric acid (see for example the works of G. Horanyi et al. Acta Chim. Acad. Sci. Hung. 1978, 98, 49–66, 367–373, Magyar Kém. Folyoirat, 1978, 84, 61–68, 217–225, 255–362, 469–475).

However, such known processes present disadvantages. Thus, (a) the nitric oxidation of glyoxal requires significant investments both for isolating glyoxylic acid and for denitrifying the washing waters, (b) the oxalic acid and the tartaric acid are little economical raw materials, (c) anodic oxidation of ethyleneglycol is little performant, and (d) the anodic glyoxal oxidation process requires the use of electrolyzers equipped with ion exchange membranes.

The Applicant however surprisingly discovered an anodic electrochemical glyoxal oxidation process permitting to prepare glyoxylic acid with good yields and good selectivity while avoiding disadvantages of known processes. The process according to the invention consists of submitting, under stirring at a temperature of between 0° C. and 70° C., an aqueous solution of glyoxal to an anodic electrochemical oxidation in an electrolyzer comprising at least one cathodic compartment containing a cathode and a catholyte, at least one anodic compartment containing an anode and an anolyte consisting of an aqueous solution of glyoxal and an electrolyte, and between these two compartments, at least one separator, such process being characterized in that the anode is doped by low quantities of metallic adatoms selected from the group comprising silver, bismuth, copper, tin, thallium.

According to another characteristic, the separator is advantageously made of sintered glass. Preferably, such sintered glass separator will have an average pore diameter of between 5 and 15 micrometers.

According to still another advantageous mode of embodiment, the separator is made of an anion exchange membrane, contray to cation exchange membranes already used in known processes of electrochemical glyoxal oxidation (see for example, French Pat. No. 2 443 517). Such an anion exchange membrane permits to prevent migration toward the cathodes of cations used for doping the anode, on the one hand, and on the other hand, to maintain the chloride ion concentration constant in the anodic compartment.

Furthermore, such anionic in membrane enhances glyoxal consumption, increases glyoxylic acid yields and provides a glyoxylic acid having little residual glyoxal.

As an example of anionic membrane that can be used in accordance with the invention, there can be cited such anionic membranes of very different origin and natures as the anionic membranes with quaternary ammonium group on polyvinylic skeleton, polystyrene, fluorinated polyvinyllidene, whether textured or not.

More particularly, there can be cited commercial membranes RAIPORE 5035 L or IONAC 3475 respectively sold by the firms:

RAI Research Corporation, 225 Marcus Boulevard Hauppage, Long Island, N.Y., 11788, United States of America, IONAC Chemical Company, Birmingham, N.J., United States of America.

The exact role exerted by such adatoms is not known but the Applicant surprisingly discovered that they favored oxidation of glyoxal and that they permitted to obtain an aqueous solution of glyoxylic acid having little untransformed glyoxal.

The anode is doped by such adatoms by electrolytic deposition either previously or in the course of the process according to the invention, starting from one of their water soluble or slightly water-soluble derivatives such as silver nitrate, bismuth III oxide, cuprous chloride, stannous chloride, thallium III nitrate. According to the invention the anode can be doped with adatoms of identical or different nature.

The preferred adatoms to dope the anode are silver and tin.

The preliminary deposition is effected by any conventional process known in itself. Generally, it is achieved in an electrolyzer with three electrodes, i.e. a reference electrode (for example, a calomel KCl saturated electrode), an auxiliary electrode of platinum and the electrode to be doped, the electrolyte of which contains in solution one or more water soluble derivatives of the adatom(s) selected to a molar concentration of $1.10^{-4}$ to $1.10^{-2}$, then the selected metal(s) are deposited electrochemically onto the electrode to be doped by using about $20\pm10$ coulombs per $cm^2$ of electrode. Such deposition can also be achieved by introducing at the beginning of the process into the anodic compartment one or more water soluble derivatives of the adatom(s) selected to a molar concentration of $1.10^{-4}$ to $1.10^{-2}$.

The process according to the invention is carried out at a temperature of between 0° C. and 70° C., preferably between 20° C. and 70° C., and advantageously at 50° C.

The electrolyzer cathode is constituted by an electricity conductive material chemically and electrochemically stable in the catholyte under the operative conditions considered. Such a material is, in particular, platinum, stainless steel.

The anode is made of platinum or vitrous carbon. The anolyte substantially contains water, glyoxal, an electrolyte and possibly low concentrations of one or more water soluble derivatives of the adatom(s) selected for doping the anode. The conventionally used electrolyte is a mineral product very soluble in water containing an anion selected from the group comprising chloride anions, nitrite anions, nitrate anions and sulfate anions. Advantageously, the electrolyte contains chloride ions supplied preferably by hydrogen chloride.

The catholyte substantially contains water and an electrolyte generally qualitatively and quantitatively identical to that present in the anolyte. However, it can differ therefrom and then contains hydroxide ions.

The molar concentrations of glyoxal in the anolyte may vary within large limits but usually there are comprised between 0.2 and 5M, advantageously they are comprised between 0.5 and 2M.

As the anodic oxidation reaction continues the anolyte is depleted of glyoxal and enriched with glyoxylic acid according to equation (1):

$$OHC\!-\!CHO + H_2O - 2e^- \rightarrow OHC\!-\!COOH + 2H^+ \quad (1)$$

In view of such equation (1), it is necessary to use 193,000 coulombs to oxidize one mole of glyoxal and such value is designated as Qth.

The glyoxylic acid formed can also be electrochemically oxidized to oxalic acid according to equation (2):

$$OHC\!-\!COOH + H_2O - 2e^- \rightarrow HOOC\!-\!COOH + 2H^+ \quad (2)$$

and finally, oxalic acid can be degraded by decarboxylating oxidation according to equation (3):

$$HOOC\!-\!COOH + H_2O - 2e^- \rightarrow 2CO^2 + H_2O + 2H^+ \quad (3)$$

Glyoxal oxidation to glyoxylic acid is therefore in competition with oxidation of glyoxylic acid formed to oxalic acid on the one hand, and on the other hand, with oxidizing decarboxylating degradation of oxalic acid possibly present.

Upon completion of the reaction, the anolyte substantially contains water, glyoxylic acid, untransformed glyoxal, electrolytes and possibly oxalic acid. The quantity of residual glyoxal is low and the use of a doped anode according to the invention permits to obtain at the end of the reaction an anolyte containing only low quantities of residual glyoxal.

The higher the ratio:

$$\rho = Q/Qth$$

(where Q=quantity of consumed electricity, an Qth=theoretical quantity of electricity), the higher the oxalic acid concentration.

The electricity density at the cathode is generally comprised between 0.1 and 10 A per dm$^2$, preferably between 0.5 and 5 A per dm$^2$ and advantageously, it is 1 A per dm$^2$.

The potential difference applied to the electrodes hereinafter designated as V is a function of the electric resistivity of the solutions contained in the various compartments, and their electrolyte concentration.

Generally, a potential difference comprised between 2 and 10 volts is sufficient for maintaining the electric density imposed upon the electrode. Usually an anolyte and a catholyte are obtained presenting a satisfactory electric resistivity by using such an electrolyte as previously defined at a concentration comprised between 0.26 and 3 as expressed in gram-liter equivalent. Such an electrolyte is notably hydrogen chloride, potassium nitrite, potassium nitrate, sodium chloride, sodium sulfate.

The preferred electrolyte is hydrogen chloride at a molar concentration of 1±0.3.

A variation in the process according to the invention consists of using an aqueous catholyte presenting a pH higher than 7, substantially constituted by water, and an alkaline metal hydroxide.

The alkaline metal hydroxide is sodium hydroxide or potassium hydroxide, preferably sodium hydroxide at a molar concentration of 1.

This modification of the process according to the invention can be realized either in a conventional electrolyzer with two compartments separated by a sintered glass diaphragm or advantageously in an electrolyzer with three compartments in series separated by a sintered glass diaphragm, with an anodic compartment containing the anode and the anolyte, a cathodic compartment containing the cathode and the catholyte, and a central intermediary compartment containing a solution identical to the catholyte used.

It will be noted with interest that diffusion of the different chemical species present in each compartment is low.

The following examples illustrate the invention without however any limitation thereof.

The cncentrations of glyoxal, glyoxylic acid and oxalic acid are expressed, save for contrary indication, in millimoles per liter of solution.

The chemical yield Rc and the electric efficiency Re are calculated with the following equations:

Chemical yield =

$$\frac{\text{Number of moles of glyoxylic acid obtained}}{\text{Number of moles of disappeared glyoxal}} \times 100$$

Electric efficiency =

$$\frac{\text{Theoretic electric quantity to obtain the dosed glyoxylic acid}}{\text{Quantity of electricity used}} \times 100$$

The electrolyzer used in Examples 1 to 13 contains two cmpartments separated by a sintered glass diaphragm with an average pore diameter of 10±5 micrometers:

a cathodic compartment of 80 cm$^3$ equipped with a platinum cathode, an anodic compartment of 120 cm$^3$ equipped with an anode with a useful area of 15 cm$^2$.

The electrolyzer used in the other Examples from 14 to 16 presents three compartments in series:

a cathodic compartment of 80 cm$^3$ equipped with a platinum cathode, a central compartment of 30 cm$^3$ separated from the anodic and cathodic compartments by a sintered glass diaphragm of an average pore diameter of 10±5 micrometers, an anodic compartment of 120 cm$^3$ equipped with magnetic stirring means and an anode with a useful area of 15 cm$^2$.

TABLE I

| EXAMPLES 1-13 - Influence of adatoms deposited on platinum anode. | | | | | | |
|---|---|---|---|---|---|---|
| OPERATIVE CONDITIONS: | | | | | | |
| Electrodes: platinum | | | Catholyte: HCl 1,1 N | | | |
| I: 1 A/dm$^2$ | | | Anolyte: HCl 1,1 N | | | |
| V: 2,8 V | | | glyoxal 0,88 M | | | |
| | Examples 1/2 | Exampl. 3/4 | Exampl. 5/7 | Exampl. 8/9 | Exampl. 10/11 | Exampl. 12/13 |
| Adatom | none | Sn | Ag | Cu | Tl | Bi |
| Nature | | SnCl$_2$ | AgNo$_3$ | CuCl | Tl(NO$_3$)$_3$ | Bi$_2$O$_3$ |

TABLE I-continued

EXAMPLES 1-13 - Influence of adatoms deposited on platinum anode.

OPERATIVE CONDITIONS:

Electrodes: platinum  
I: 1 A/dm$^2$  
V: 2,8 V

Catholyte: HCl 1,1 N  
Anolyte: HCl 1,1 N  
glyoxal 0,88 M

| | Examples 1/2 | | Exampl. 3/4 | | Exampl. 5/7 | | | Exampl. 8/9 | | Exampl. 10/11 | | Exampl. 12/13 | |
|---|---|---|---|---|---|---|---|---|---|---|---|---|---|
| Quantity mmol/l | | | 1.2 | | 1.35 | | | 2.3 | | 0.6 | | 0.5 | |
| Temperature °C. | 20 | 50 | 20 | 50 | 20 | 50 | 50 | 20[1] | 50[2] | 20 | 50 | 50 | 50[3] |
| Q/Qth | 1.2 | 1.2 | 1.23 | 1.2 | 1.01 | 1.2 | 1.65 | 1.28 | 1.2 | 1.15 | 1.27 | 1.22 | 1.25 |
| Results: | | | | | | | | | | | | | |
| residual glyoxal | 151 | 99 | 60 | 17 | 90 | 35 | 7 | 120 | 51 | 120 | 26 | 65 | 52 |
| glyoxylic acid | 463 | 482 | 446 | 554 | 500 | 613 | 473 | 594 | 1200 | 500 | 540 | 513 | 540 |
| oxalic acid | 38 | 8.5 | 77 | 64 | 23 | 77 | 55 | 44 | 200 | 44 | 111 | 66 | 77 |
| chemical yield | 63.5 | 62 | 55 | 63 | 63 | 72.5 | 54 | 78 | 72 | 66 | 63 | 63 | 65 |
| electric efficiency. | 44 | 46 | 41 | 52 | 57 | 59 | 31 | 53 | 59 | 50 | 50 | 50 | 49 |

NOTES:
[1] Deposition of copper adatom was effected from cuprous chloride in another cell before electrolysis in the presence of glyoxal.
[2] Such example was realized with an anolyte containing hydrochloric acid 1.1 N and glyoxal 1,71 M.
[3] Deposition of bismuth adatom was effected from bismuth III oxide in another cell before electrolysis in the presence of glyoxal.

In all the other examples the adatom was deposited onto the platinum anode.

Such Table shows that by carrying out the invention with differing adatoms glyoxylic acid is obtaind having little residual glyoxal as compared to the process carried out under analogous conditions without anode doping.

TABLE II

EXAMPLES 14 to 16

OPERATIVE CONDITIONS:

I = 1 A/dm$^2$  
Catholyte = NaOH 1N  
Anolyte = HCl 1,1 N  
glyoxal 0,860 M

| | Example 14 | Example 15 | Example 16 |
|---|---|---|---|
| Anode | Platinum | Platinum | Platinum |
| Adatom | none | none | Ag$^{+(1)}$ |
| Temperature °C. | 20 | 50 | 50 |
| V volts | 3 | 2.8 | 2.8 |
| Q/Qth | 1.22 | 1.22 | 1.22 |
| Results: | | | |
| residual glyoxal | 146 | 77.5 | 17.2 |
| glyoxylic acid | 432 | 676 | 676 |
| oxalic acid | 33 | 68 | 64 |
| chemical yield | 60.5% | 86.4% | 80.2% |
| electric efficiency | 41% | 64% | 64% |

[1] Anode doping was effected by introducing at the beginning of the electrolysis 14 mg of silver nitrate inot the anodic compartment.

It appears from the examination of this Table that by applying the modified embodiment of the invention there is also obtained a catholyte containing ions OH$^-$ and a glyoxylic acid having little residual glyoxal therein.

The following examples illustrate another modified form of embodiment of the invention wherein an electrolyzer is used comprising two compartments separated by a commercial anionic membrane; these two compartments have a volume of about 25 cm$^3$ and they are respectively provided with an anode and a cathode of platinum, magnetic stirring means and a refrigerant to prevent water evaporation when the tests are carried out at a temperature higher than 20° C.

The results obtained are contained in the following Table III hereinbelow:

TABLE III

Examples 17-20  
Influence of adatoms deposited on the anode and of an ion exchange membrane.

| | Examples | | | |
|---|---|---|---|---|
| | 17 | 18 | 19 | 20 |
| OPERATIVE CONDITIONS: | | | | |
| Electrodes | platinum | | | |
| Electrolyte | HCl 1,1 N | | | |
| Intensity I A/dm$^2$ | 1 | | | |
| Voltage V | 2.5-2.8 | | | |
| Initial volume cm$^3$ | 20 | | | |
| Final volume cm$^3$ | 21-22 | | | |
| Membrane anionic membrane | RAIPORE 5035 L | | | |
| Adatom | none | Sn$^{++}$ | Ag$^+$ | |
| nature | | SnCl$_2$ | AgNO$_3$ | |
| quantity mmol/l | | 1.11 | 1.18 | |
| Temperature °C. | 20 | 20 | 20 | 50 |
| Q/Qth | 1.20 | 1.20 | 1.21 | 1.21 |
| Electricity quantity C | 4790 | 4150 | 4180 | 4180 |
| Initial glyoxal mmol/l | 1035 | 895 | 895 | 895 |
| Results | | | | |
| Residual glyoxal mmol/l | 145 | 60.5 | 57 | 17 |
| Glyoxylic acid mmol/l | 650 | 575 | 585 | 629 |
| Oxalic acid mmol/l | 57 | 72 | 71 | 79 |
| Final chlorides | 1.1 N | | | |
| Chemical yield % | 73 | 69 | 70 | 72 |
| Electric efficiency % | 53 | 53 | 54 | 58 |

Upon examining such Table it can be noted that simultaneous use of an anionic membrane and a doped anode leads to chemical yields and electric efficiencies higher than those obtained with the sintered glass separator. Moreover, comparison of Example 17 with Examples 18-20 shows the favorable influence of the use of a doped anode on the residual glyoxal rates.

It will be understood that this invention was only described in a purely illustrative and not at all limitative manner and that any useful modification can be brought thereto in particular as regards technical equivalences without however departing from its scope as defined in the appended claims.

We claim:

1. In a process for preparation of glyoxylic acid by electrochemical oxidation of glyoxal in aqueous solution, at a temperature comprised between 0° C. and 70° C., in an electrolyzer comprising at least one cathodic compartment containing a cathode and a catholyte, at least one anodic compartment containing an anode and an anolyte consisting of an aqueous solution of glyoxal and an electrolyte and at least one separator between both of these compartments, the improvement wherein said anode is doped by metallic adatoms selected from the group comprising silver, bismuth, copper, tin and thallium.

2. The improvement according to claim 1, wherein said separator is made of sintered glass.

3. The improvement according to claim 1, wherein said separator is an anionic membrane.

4. The improvement according to claim 1, wherein the catholyte is an aqueous solution of an alkaline metal hydroxide.

5. The improvement according to claim 1, wherein said anolyte is a glyoxal solution in hydrochloride acid $1\pm0.3N$.

6. The improvement according to claim 4, wherein said catholyte is a normal solution of sodium hydroxide.

* * * * *